United States Patent

Nonaka

(10) Patent No.: US 9,901,316 B2
(45) Date of Patent: Feb. 27, 2018

(54) RADIATION IMAGING SYSTEM, RADIATION IMAGING APPARATUS, CONTROL METHODS THEREFOR, AND NON-TRANSITORY COMPUTER-READABLE STORAGE MEDIUM

(71) Applicant: CANON KABUSHIKI KAISHA, Tokyo (JP)

(72) Inventor: Hideki Nonaka, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 229 days.

(21) Appl. No.: 14/802,320

(22) Filed: Jul. 17, 2015

(65) Prior Publication Data

US 2016/0022231 A1   Jan. 28, 2016

(30) Foreign Application Priority Data

Jul. 24, 2014   (JP) ................... 2014-151044

(51) Int. Cl.
 *G01J 1/42*    (2006.01)
 *A61B 6/00*    (2006.01)

(52) U.S. Cl.
 CPC .......... *A61B 6/4405* (2013.01); *A61B 6/4411* (2013.01); *A61B 6/462* (2013.01); *A61B 6/563* (2013.01); *A61B 6/566* (2013.01)

(58) Field of Classification Search
 CPC ..... A61B 6/4405; A61B 6/4411; A61B 6/566; A61B 6/563; A61B 6/462
 USPC ......................... 250/393, 394, 395
 See application file for complete search history.

(56) References Cited

U.S. PATENT DOCUMENTS

2013/0329860 A1\*  12/2013  Nonaka ............... G06F 19/3418
378/91

FOREIGN PATENT DOCUMENTS

JP   2009-186439 A   8/2009
JP   2010-268822 A   12/2010

\* cited by examiner

*Primary Examiner* — David Porta
*Assistant Examiner* — Meenakshi Sahu
(74) *Attorney, Agent, or Firm* — Fitzpatrick, Cella, Harper & Scinto

(57) ABSTRACT

A radiation imaging system comprises a radiation generation unit configured to generate radiation, and at least one imaging unit configured to detect radiation from the radiation generation unit and obtain a radiation image, the imaging unit including a control unit configured to control to operate in one of a first operation mode of capturing the radiation image and controlling the radiation imaging system and a second operation mode of capturing the radiation image.

11 Claims, 3 Drawing Sheets

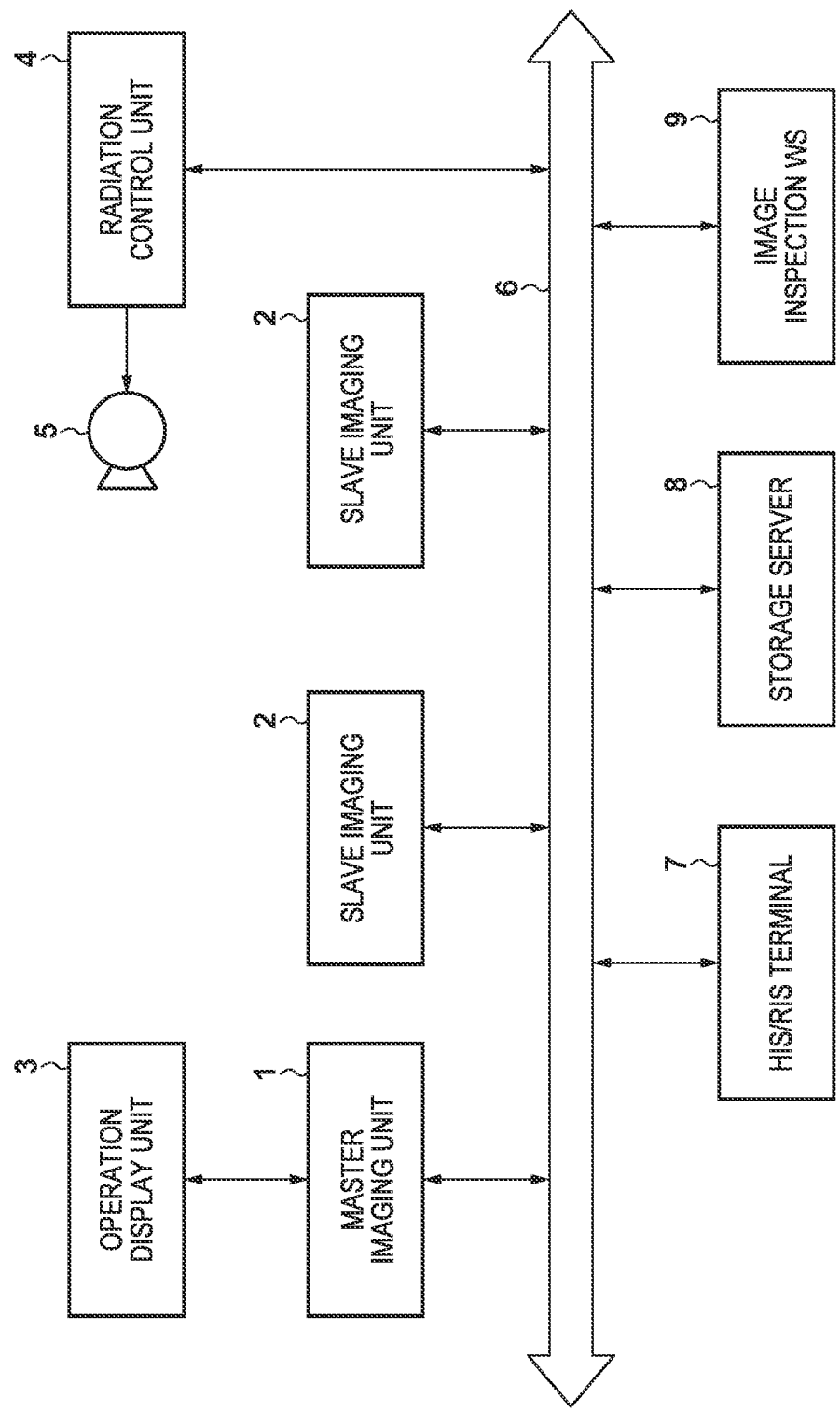

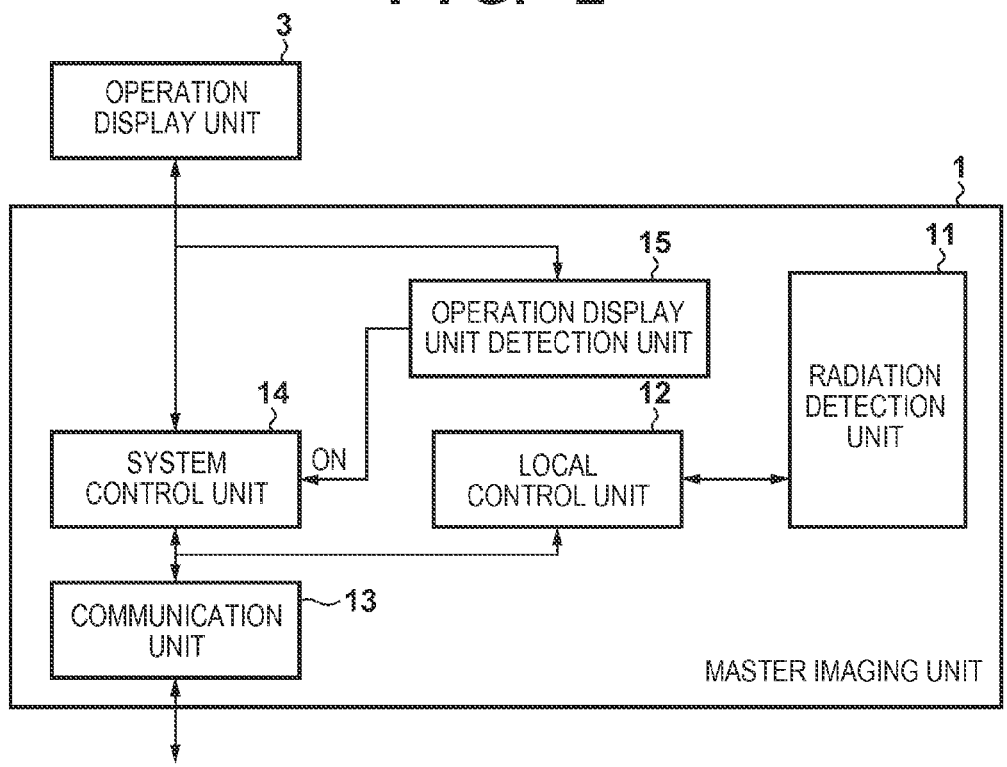
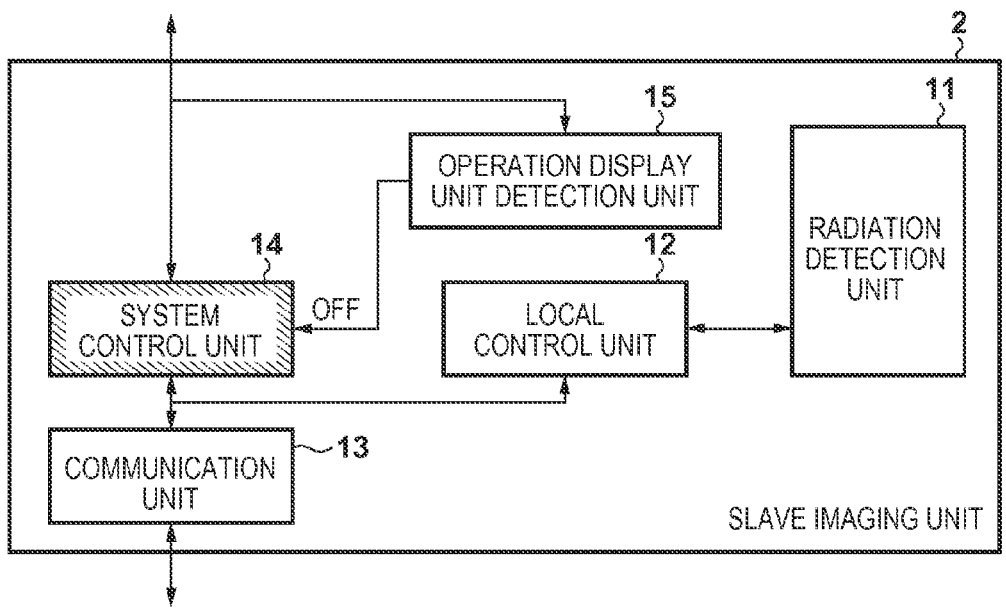

RADIATION IMAGING SYSTEM, RADIATION IMAGING APPARATUS, CONTROL METHODS THEREFOR, AND NON-TRANSITORY COMPUTER-READABLE STORAGE MEDIUM

BACKGROUND OF THE INVENTION

Field of the Invention

The present invention relates to a radiation imaging system, a radiation imaging apparatus, control methods therefor, and a non-transitory computer-readable storage medium.

Description of the Related Art

A radiation imaging system includes a radiation generation apparatus for generating radiation, and an imaging unit for generating a radiation image by detecting radiation. In recent years, products each of which uses a flat panel detector (FPD) as an imaging unit have become widespread. Detection elements (pixels) are arranged on the detector surface of an FPD in a matrix pattern, and the FPD accumulates signal charges generated for the respective pixels in accordance with the detection amount of radiation, and then A/D-converts the signal charges to obtain digital data. This digital data undergoes image processing and is used for diagnosis.

In general, in a radiation imaging system using imaging units, a system control unit is prepared to set the operations of the imaging units, input imaging order information such as an imaging portion and a patient name, and display a captured image, and all the imaging units exiting in the system are controlled by the system control unit. An operation unit and display unit are connected to the system control unit. The operation unit is used to operate the imaging units, and the display unit is used to display a radiation image output from the imaging unit. In general, a PC is used as the system control unit, an input device such as a keyboard and mouse is used as the operation unit, and a display device such as a liquid crystal display is used as the display unit.

After setting imaging conditions such as the exposure amount of radiation in a radiation generation apparatus, selecting an imaging unit to be used, and inputting imaging order information such as an imaging portion and the name and height/weight of a patient to the system control unit, a radiological technician who performs imaging of the patient guides the patient to the imaging unit, and performs radiation imaging based on pressing of an exposure button.

However, for example, when imaging in a standing posture which is supposed to be performed is urgently changed to imaging in a supine posture because the patient cannot support his/her body, or when imaging in a large square size which is supposed to be performed is changed to imaging in a half size because the body build of the patient is large, it may be necessary to change the imaging order information. Conventionally, the radiological technician needs to move to the system control unit, and change the imaging order.

To solve this problem, Japanese Patent Laid-Open No. 2010-268822 discloses a technique of allowing modification of imaging order information of a system control unit from an operation unit without moving to the system control unit by connecting the operation unit communicable with the system control unit to the imaging unit in order to reduce the above complicated operation.

In the technique described in Japanese Patent Laid-Open No. 2010-268822, however, the system control unit is required, and thus conveyance and installation of the radiation imaging system become complicated, thereby disabling the portability of the overall system from improving, and increasing the system cost.

The present invention has been made in consideration of the above problems, and provides a technique of reducing the system cost while improving the portability of the overall radiation imaging system.

SUMMARY OF THE INVENTION

According to one aspect of the present invention, there is provided a radiation imaging system comprising a radiation generation unit configured to generate radiation, and at least one imaging unit configured to detect radiation from the radiation generation unit and obtain a radiation image, the imaging unit including a control unit configured to control to operate in one of a first operation mode of capturing the radiation image and controlling the radiation imaging system and a second operation mode of capturing the radiation image.

Further features of the present invention will become apparent from the following description of exemplary embodiments with reference to the attached drawings.

BRIEF DESCRIPTION OF THE DRAWINGS

FIG. 1 is a view showing an example of the configuration of a radiation imaging system according to an embodiment of the present invention;

FIG. 2 is a block diagram showing an example of an internal arrangement when an imaging unit operates as a master imaging unit according to the embodiment of the present invention;

FIG. 3 is a block diagram showing an example of an internal arrangement when the imaging unit operates as a slave imaging unit according to the embodiment of the present invention.

DESCRIPTION OF THE EMBODIMENTS

Figure 4:
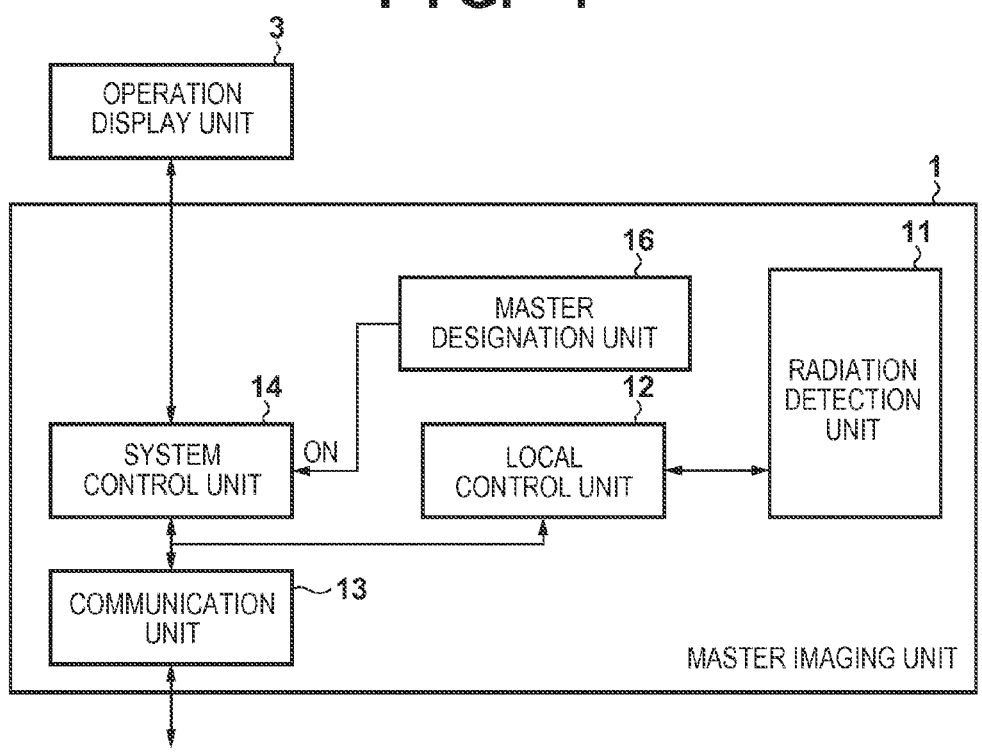
FIG. 4 is a block diagram showing another example of the internal arrangement when the imaging unit operates as a master imaging unit according to the embodiment of the present invention.

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

<1. Configuration of Radiation Imaging System>

FIG. 1 is a view showing an example of the configuration of a radiation imaging system according to the embodiment of the present invention. The radiation imaging system includes a master imaging unit 1, a slave imaging unit 2, an operation display unit 3, a radiation control unit 4, a radiation tube 5, a communication path 6, an HIS (Hospital Information System)/RIS (Radiology Information System) terminal 7, a storage server 8, and an image inspection workstation 9. Note that the radiation control unit 4 and radiation tube 5 will be collectively referred to as a radiation generation unit hereinafter.

The master imaging unit 1 and one or more slave imaging units 2 are communicably connected via the communication path 6. The communication path 6 may be wired or wireless. The operation display unit 3 is connected to the master imaging unit 1. The radiation control unit 4 is connected to the communication path 6 in addition to the master imaging unit 1 and slave imaging unit 2, and the radiation tube 5 performs irradiation with radiation in accordance with an instruction of the radiation control unit 4. Similarly, the HIS/RIS terminal 7, the storage server 8 for saving a captured image, and the image inspection workstation 9 for performing image processing on the captured image, and performing an operation for finally using the image for diagnosis are connected to the communication path 6.

The master imaging unit 1 and the slave imaging unit 2 have different names due to their different operation modes but the devices themselves are completely the same. When it is not necessary to discriminate between the master imaging unit 1 and the slave imaging unit 2, they will be referred to as imaging units hereinafter.

<2. Internal Arrangement of Imaging Unit>

The internal arrangement of the imaging unit will be explained. FIG. 2 is a block diagram showing the internal arrangement of the master imaging unit 1. FIG. 3 is a block diagram showing the internal arrangement of the slave imaging unit 2. The imaging unit includes a radiation detection unit 11, a local control unit 12, a communication unit 13, a system control unit 14, and an operation display unit detection unit 15.

The radiation detection unit 11 includes a scintillator, a photodetector array, a driving circuit, and an A/D conversion circuit (none are shown). In the scintillator, high-energy radiation excites the matrix material of a phosphor to generate luminescence by energy upon recombination. The photodetector array is arranged adjacent to the scintillator. The photodetector array has a structure obtained by arranging, in a matrix pattern, pixels for converting photons into electric energy and accumulating it. The accumulated electric energy is sequentially extracted by the driving circuit, and output as digital data corresponding to the incident radiation dose by the A/D conversion circuit. Note that the arrangement of the radiation detection unit 11 is not limited to this and, for example, a detector having direct sensitivity to radiation may be used.

The local control unit 12 controls an operation in the imaging unit. More specifically, the local control unit 12 controls the operation of the radiation detection unit 11 to perform the imaging operation of a radiation image, associates imaging order information, which has been received from an external apparatus via the communication unit 13 before imaging, with the radiation image after imaging, and outputs the radiation image to the storage server 8 for saving the image and the image inspection workstation 9 for performing image processing and the like to generate a final image to be used for diagnosis.

The communication unit 13 communicates with an external apparatus to receive imaging order information from the external apparatus and transmit a captured radiation image to the external apparatus.

The system control unit 14 controls, by including itself, the overall radiation imaging system in which the imaging unit exists. For example, the system control unit 14 performs an operation of setting the operation of the imaging unit such as input of imaging order information, and the display processing of a captured image. Processing executed by the system control unit 14 requires an input/output device for inputting information and outputting an image but the operation display unit 3 provided outside the imaging unit is used as the input/output device. The operation display unit 3 is connected to the system control unit 14 of the master imaging unit 1 (see FIG. 2), displays a console screen for controlling the overall radiation imaging system and an image captured by the imaging unit, and accepts an operation and character input by buttons displayed on the console. For this application purpose, a liquid crystal touch panel display is preferable. Alternatively, a mobile PC or tablet terminal including such display may be used.

The operation display unit detection unit 15 detects that the operation display unit 3 is connected to the imaging unit. Upon detecting that the operation display unit 3 is connected to the imaging unit, the operation display unit detection unit 15 enables the system control unit 14.

The radiation imaging system according to this embodiment includes two types of imaging units, that is, the master imaging unit 1 and the slave imaging unit 2, but the internal arrangements of the imaging units are completely the same. Among the plurality of imaging units existing in the imaging system, one arbitrary imaging unit serves as the master imaging unit 1, and the other imaging units serve as the slave imaging units 2, thereby forming the system.

In the initial state of the radiation imaging system, all the imaging units serve as the slave imaging units 2. Subsequently, the operation display unit 3 is connected. When the operation display unit 3 is connected to one arbitrary slave imaging unit 2, the operation display unit detection unit 15 detects that the operation display unit 3 is connected to itself, enables the system control unit 14, and switches the operation mode to the master imaging unit 1. To the contrary, when the operation display unit 3 is not connected, the operation display unit detection unit 15 disables the system control unit 14, and switches the operation mode to the slave imaging unit 2. The imaging unit and the operation display unit 3 may be connected by wired or wireless connection. If wireless connection is used and a plurality of imaging units exist, a connection between the operation display unit 3 and one specific imaging unit is established.

As a connection establishment method, a method of connecting the operation display unit 3 to an imaging unit having the shortest distance to the operation display unit 3, a method of connecting the operation display unit 3 to an imaging unit having the highest reception strength, a method of connecting the operation display unit 3 to an imaging unit for which a connection establishment operation has been performed first, or a method of connecting the operation display unit 3 to an imaging unit additionally designated by the user may be used. Since all the imaging units have the same internal arrangement, when the operation display unit 3 is connected to any of the imaging units, this causes no difference in the system operation or manipulation. Especially for wireless connection, an imaging unit as a connection destination may be dynamically changed to ensure a more preferable wireless connection status.

The operation display unit detection unit 15 may be configured to detect a wired connection by an electrical or mechanical switch, or detect a connection by monitoring the status of communication between the system control unit 14 and the operation display unit 3 regardless of whether the connection is wired or wireless.

As shown in FIG. 4, instead of the operation display unit detection unit 15, a master designation unit 16 may be provided to allow the user to designate an arbitrary imaging unit as the master imaging unit 1. For example, when the user turns on the electrical or mechanical switch, the master designation unit 16 enables the system control unit 14 to start an operation as the master imaging unit 1. This is useful to operate the radiation imaging system even when no operation display unit 3 exists.

<3. Practical Processing of Imaging Unit>

An imaging unit serving as the master imaging unit 1 notifies all the slave imaging units 2 existing in the radiation imaging system of a message indicating that a master mode operation is in progress. Upon receiving the message, each slave imaging unit 2 sets, as an image data transmission destination at the time of subsequent imaging, the master imaging unit 1 as a message transmission source.

Prior to imaging, the radiological technician operates the screen of the operation display unit 3 to input radiation imaging conditions and imaging order information such as an imaging portion and the name and height/weight of a patient. The system control unit 14 of the master imaging unit 1 distributes the input imaging order information to all the imaging units including itself, and the local control unit 12 of each imaging unit holds the information. The settings about the radiation imaging conditions are also set in the radiation control unit 4. Note that the radiological technician manually inputs the imaging order information from the operation display unit 3 in this example, but the HIS/RIS terminal 7 communicably connected to the communication path 6 can distribute the imaging order information. As a distribution path at this time, the master imaging unit 1 may receive the imaging order information from the HIS/RIS terminal 7 and then distribute it to each slave imaging unit or the HIS/RIS terminal 7 may distribute the imaging order information directly to all the imaging units.

Upon receiving the imaging order information, the local control unit 12 of each of all the imaging units executes a preparation operation to set the radiation detection unit 11 in an imaging enable state. After that, the radiation detection unit 11 is set in an imaging standby state. In this state, since the imaging order information has been distributed to all the imaging units and the radiation detection units 11 are in the imaging standby state, all the imaging units can be used for imaging. For example, even when imaging in a standing posture is changed to imaging in a supine posture or the imaging unit is changed to that having a large imaging region because the body build of a patient is large, an additional operation is not necessary and imaging can be performed using the desired imaging unit without any change.

The radiological technician selects an arbitrary imaging unit appropriate for imaging to fix the posture of the patient, and irradiates the patient with radiation from the radiation tube 5 by pressing the exposure button of the radiation control unit 4, thereby performing imaging. Electric energy for forming a captured image of the patient by irradiation with radiation is accumulated in the radiation detection unit 11. To read out the electric energy, it is necessary to perform the readout operation after confirming completion of irradiation with radiation. For example, the imaging unit may detect the radiation irradiation state, and shift the radiation detection unit 11 from the accumulation operation mode during irradiation to a readout mode subsequent to the accumulation operation mode. That is, when irradiation with radiation is performed for an arbitrary imaging unit, the imaging unit itself detects the incidence of radiation. These processes are performed by the local control unit 12. Upon detecting the incidence of radiation, the local control unit 12 stands by for the end of irradiation with radiation, and then reads out image data from the radiation detection unit 11. The readout captured image data is associated with the imaging order information by performing processing of, for example, embedding the imaging order information received prior to imaging in the header portion of the captured image data and outputting the resultant data. The associated captured image data is transmitted to the system control unit 14 of the master imaging unit 1, and displayed on the operation display unit 3.

At this time, since the associated imaging order information has been distributed to all the imaging units, the pieces of imaging order information of the same contents remain in the imaging units which have not been used for imaging. If the next imaging operation is performed without any change, this imaging order information is associated with another image. To cope with this, synchronization for deleting or disabling the information is required for all the imaging units. To synchronize the pieces of imaging order information, for example, upon completion of associating the acquired image with the imaging order information, the imaging completion notification of the order may be distributed to the local control units 12 of all the imaging units. Alternatively, the local control unit 12 of the imaging unit used for imaging may notify the system control unit 14 of the master imaging unit 1 of completion of imaging of the order, and upon receiving the notification, the system control unit 14 of the master imaging unit 1 may distribute the notification to the local control units 12 of all the imaging units including itself.

Alternatively, since the imaging unit used for imaging transmits the captured image data to the system control unit 14 of the master imaging unit 1, upon receiving the data, the system control unit 14 of the master imaging unit 1 may read out the imaging order information added to the received captured image data, and distribute the imaging completion notification of the corresponding imaging order information to the local control units 12 of all the imaging units including itself. Upon receiving the imaging completion notification, the local control unit 12 of the imaging unit deletes the corresponding imaging order information from the memory area, or adds information indicating that the imaging order information is unusable.

When the HIS/RIS terminal 7 distributes the imaging order information, and image display is not required, the master imaging unit 1 may be unnecessary and only the slave imaging units 2 may create the system. This is usable especially for a use method that emphasizes the portability, for example, at the time of carrying the system outside a hospital and using it or at the time of loading a mobile radiation apparatus.

As described above, according to the embodiment of the present invention, the master imaging unit 1 and the plurality of slave imaging units 2 are communicably connected via the communication path 6. The operation display unit 3 is connected to the master imaging unit 1. The radiation control unit 4 is also connected to the communication path 6, and the radiation tube 5 performs irradiation with radiation in accordance with an instruction of the radiation control unit 4. Similarly, the HIS/RIS terminal 7, storage server 8, and image inspection workstation 9 are connected to the communication path 6. The imaging order information is distributed from the operation display unit 3 or the HIS/RIS terminal 7 to all the imaging units. Upon receiving the imaging order information, each of all the imaging units sets the radiation detection unit 11 in the imaging standby state to stand by for execution of radiation imaging. When radiation imaging is executed, the imaging order information and a captured radiation image are associated with each other in the imaging unit used for imaging, and then output. The imaging order information used to execute radiation imaging is deleted from each of all the imaging units or inhibited from being used after imaging.

According to the present invention, by distributing the imaging order information to all the imaging units of the system, and associating a captured image and the imaging order information with each other in the imaging unit used for imaging immediately after imaging, it is possible to implement an imaging system in which imaging can be performed using an arbitrary imaging unit existing in the imaging system and the imaging order information and the captured image are reliably associated with each other.

Furthermore, since a predetermined imaging unit in the imaging system serves as a function of controlling the imaging system, it is possible to implement the imaging system that is excellent in the portability of the overall imaging system, can be carried and used outside a hospital at the time of an accident/disaster or at the time of visiting a patient convalescing at home, and can readily form an imaging system for a hospital round by loading an imaging unit to the mobile radiation apparatus.

Furthermore, it is possible to reduce the system cost while improving the portability of the overall radiation imaging system.

In another embodiment, the master imaging unit 1 and the slave imaging unit 2 according to the above-described embodiment are operated by switching the master function and slave function, as needed. For example, when there are two imaging units in the radiation imaging system, the master imaging unit 1 is used in another radiation imaging system, and thus the association between the master imaging unit 1 and the system is canceled. If a cancel instruction is issued, the slave imaging unit 2 functions as a master imaging unit. In another example, if information about an imaging unit to be used is associated with each of a plurality of imaging orders, the imaging unit having the largest imaging count may be selected as the master imaging unit 1. It is possible to implement an efficient operation by setting, in a power saving mode, an imaging unit that is not to be used. To the contrary, by selecting, as the master imaging unit 1, an imaging unit having the smallest imaging count, or an imaging unit having the smallest imaging count among imaging units having a imaging count of 1 or more, the imaging unit having a light load takes charge of processing of managing or controlling the radiation imaging system, thereby improving the robustness of the system.

In the above-described processing of selecting a master imaging unit, the system control unit 14 of an imaging unit that serves as a master imaging unit at a given time selects a master imaging unit based on imaging order information. If information about an imaging unit to be used for the imaging order is associated, the estimated imaging count of each imaging unit is calculated based on the information about the imaging unit to be used, and a master imaging unit is selected based on the calculation result, as described above. Alternatively, the operation display unit 3 may execute the above-described selection processing. In another example, the master imaging unit 1 may be selected in response to acceptance of an operation input for the operation display unit 3 to select one of the imaging units.

According to still another embodiment, each imaging unit transmits, directly to the operation display unit 3 or the like, information such as radiation image data obtained by imaging regardless of whether the imaging unit is the master imaging unit 1 or the slave imaging unit 2. In this case, the master imaging unit 1 performs the first control operation of storing, in the memory of the master imaging unit 1, a radiation image obtained by the radiation detection unit 11 of the master imaging unit 1 and identification information of an imaging order corresponding to the radiation image among a plurality of imaging orders in association with each other, and the second control operation of storing, in the memory, information indicating completion of imaging for an imaging order corresponding to imaging by the slave imaging unit 2 among the plurality of imaging orders and identification information indicating the imaging order in association with each other. These control operations may be executed by the local control unit 12 or the system control unit 14. Alternatively, the first control operation may be performed by the local control unit 12 and the second control operation may be performed by the system control unit 14.

The communication unit 13 of the slave imaging unit 2 externally transmits information indicating that imaging corresponding to one of the plurality of imaging orders has been performed. At this time, the information indicating that imaging has been performed and the ID of the slave imaging unit 2 or the ID of the imaging order may be associated with each other, and then externally transmitted. If there is no ID information of the slave imaging unit 2 or the like, the reception side of the information specifies the transmission source apparatus based on the MAC address and IP address of the transmission source of the information. This external apparatus is, for example, the master imaging unit 1. In another example, the slave imaging unit 2 may transmit the information directly to the HIS/RIS terminal 7 or another relay terminal instead of the master imaging unit 1. In this case, however, the master imaging unit 1 additionally receives information indicating that imaging has been performed.

According to still another embodiment, a control apparatus may be additionally provided to integrally manage the master imaging unit 1 or the slave imaging unit 2. In this case, the imaging order information and information indicating the progress status of the imaging order are managed not only by the master imaging unit 1 or the slave imaging unit 2 but also by the control apparatus. This can accurately manage the information. The operation display unit 3 may function as the control apparatus.

According to the present invention, it is possible to reduce the system cost while improving the portability of the overall radiation imaging system.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-Ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-151044, filed Jul. 24, 2014, which is hereby incorporated by reference wherein in its entirety.

What is claimed is:

1. A radiation imaging system comprising:
   a plurality of imaging apparatuses, each of which performs an imaging operation for detecting radiation irradiated from a radiation generation unit and obtaining a radiation image; and
   an input/output apparatus that performs input of imaging order information for the imaging operation and output of the radiation image,
   each of the plurality of imaging apparatuses comprising:
   a first control unit configured to control a whole radiation imaging system in accordance with the imaging order information; and
   a second control unit configured to control an imaging operation in the imaging apparatus in accordance with the imaging order information received from the first control unit,
   wherein the first control unit of one designated imaging apparatus of the plurality of imaging apparatuses is activated, and the first control unit of another non-designated imaging apparatus of the plurality of imaging apparatuses is inactivated.

2. The system according to claim 1, wherein the input/output apparatus comprises:
   an operation display unit configured to display the radiation image captured by the plurality of imaging apparatuses, and accept input of the imaging order information,
   wherein each of the plurality of imaging apparatuses further includes a detection unit configured to detect a connection to the operation display unit, and
   wherein the first control unit is activated by being set to be activated by the detection unit in a case where the connection to the operation display unit is detected by the detection unit, and the first control unit is inactivated by not being set to be activated by the detection unit in a case where the connection to the operation display unit is not detected by the detection unit.

3. The system according to claim 2, wherein the first control unit associates the imaging order information with the radiation image captured by one imaging apparatus of the plurality of the imaging apparatuses.

4. The system according to claim 2, wherein each of the plurality of imaging apparatuses further includes a notification unit configured to notify the other imaging apparatus of the imaging order information obtained from the operation display unit.

5. The system according to claim 4, wherein after the first control unit associates the imaging order information with the radiation image, the notification unit notifies the other imaging apparatus of completion of an imaging operation based on the imaging order information.

6. The system according to claim 5, wherein upon receiving the notification indicating completion of the imaging operation based on the imaging order information, the other imaging apparatus performs one of an operation of deleting the imaging order information and an operation of inhibiting the imaging order information from being used.

7. The system according to claim 1, wherein each of the plurality of imaging apparatuses further includes a radiation detection unit configured to detect the radiation irradiated from the radiation generation unit and to obtain the radiation image, and
   wherein the second control unit controls the imaging operation by further controlling an accumulation operation during irradiation with radiation and a readout operation after the accumulation operation based on detection of incidence of radiation on the radiation detection unit.

8. The system according to claim 1, wherein each of the plurality of imaging apparatuses further includes a designation unit configured to accept designation from a user, and
   wherein the first control unit is activated by being set to be activated by the designation unit in a case where the designation is accepted by the designation unit, and is inactivated by not being set to be activated by the designation unit in a case where the designation is not accepted by the designation unit.

9. An imaging apparatus used for a radiation imaging system comprising:
   a plurality of imaging apparatuses, each of which performs an imaging operation for detecting radiation irradiated from a radiation generation unit and obtaining a radiation image; and
   an input/output apparatus that performs input of imaging order information for the imaging operation and output of the radiation image,
   the imaging apparatus comprising:
   a first control unit configured to control an entirety of the radiation imaging system in accordance with the imaging order information; and
   a second control unit configured to control an imaging operation in the imaging apparatus in accordance with the imaging order information received from the first control unit,
   wherein the first control unit is activated in a case where a designation is accepted, and the first control unit is inactivated in a case where the designation is not accepted.

10. A control method for a radiation imaging system comprising a plurality of imaging apparatuses, each of which performs an imaging operation for detecting radiation irradiated from a radiation generation unit and obtaining a radiation image, and an input/output apparatus that performs input of imaging order information for the imaging operation and output of the radiation image, each of the plurality of imaging apparatuses comprising a first control unit configured to control a whole radiation imaging system in accordance with the imaging order information and a second control unit configured to control an imaging operation in the imaging apparatus in accordance with the imaging order information received from the first control unit, said method comprising:
   activating the first control unit of one designated imaging apparatus of the plurality of imaging apparatuses and inactivating the first control unit of another non-designated imaging apparatus of the plurality of imaging apparatuses.

11. A non-transitory computer-readable storage medium storing a computer program for causing a computer to execute the steps of a control method for a radiation imaging system comprising a plurality of imaging apparatuses, each of which performs an imaging operation for detecting radiation from a radiation generation unit and obtaining a radiation image, and an input/output apparatus that performs input of imaging order information for the imaging operation and output of the radiation image, each of the plurality of imaging apparatuses comprising a first control unit configured to control a whole radiation imaging system in accordance with the imaging order information, and a second control unit configured to control an imaging operation in the imaging apparatus in accordance with the imaging order information received from the first control unit, wherein the method comprises:

activating the first control unit of one designated imaging apparatus of the plurality of imaging apparatuses and inactivating the first control unit of another non-designated imaging apparatus of the plurality of imaging apparatuses.

* * * * *